(12) United States Patent  (10) Patent No.: US 6,431,189 B1
Deibert  (45) Date of Patent: Aug. 13, 2002

(54) APPARATUS FOR AND METHOD OF DISINFECTING HANDS

(75) Inventor: Ronald Henry Deibert, Calgary (CA)

(73) Assignee: 700303 Alberta Ltd., Calgary (CA)

( * ) Notice: Subject to any disclaimer, the term of this patent is extended or adjusted under 35 U.S.C. 154(b) by 0 days.

(21) Appl. No.: 09/335,761

(22) Filed: Jun. 18, 1999

Related U.S. Application Data

(63) Continuation-in-part of application No. 08/867,028, filed on Jun. 2, 1997, now abandoned.

(51) Int. Cl.$^7$ ................................................ B08B 3/02
(52) U.S. Cl. ........................... 134/57 R; 134/102.2; 134/182; 134/199; 134/113; 128/366; 604/289
(58) Field of Search ................. 134/102.2, 179, 134/182, 199, 201, 113, 57 R, 58 R; 128/366; 604/289

(56) References Cited

U.S. PATENT DOCUMENTS

| | | | |
|---|---|---|---|
| 2,641,771 A | 6/1953 | Schiro | ........................ 134/199 |
| 2,814,081 A | 11/1957 | Stevenson | |
| 3,059,815 A | 10/1962 | Parsons, Jr. | |
| 3,220,424 A | * 11/1965 | Nelson | |
| 3,481,687 A | 12/1969 | Fishman | ..................... 134/184 |
| 3,699,984 A | * 10/1972 | Davis | |
| 3,744,149 A | 7/1973 | Helbling | |
| 3,757,806 A | * 9/1973 | Bhaskar et al. | |
| 3,918,987 A | * 11/1975 | Kopfer | |
| 3,992,730 A | * 11/1976 | Davis | |
| 4,020,856 A | * 5/1977 | Masterson | |
| 4,130,123 A | 12/1978 | Wines, Jr. et al. | ........ 134/56 R |
| 4,219,367 A | * 8/1980 | Cary, Jr. et al. | |
| 4,295,233 A | * 10/1981 | Hinkel et al. | |
| 4,402,331 A | * 9/1983 | Taldo et al. | |
| 4,436,113 A | 3/1984 | Finger | ......................... 137/565 |
| 4,670,010 A | * 6/1987 | Dragone | |
| 4,769,863 A | 9/1988 | Trgg et al. | |
| 4,817,651 A | * 4/1989 | Crisp et al. | |
| 4,834,336 A | 5/1989 | Byzitter | .................... 134/104.1 |
| 4,925,495 A | 5/1990 | Crisp et al. | |
| 4,942,631 A | 7/1990 | Rosa | |
| 5,074,322 A | * 12/1991 | Jaw | |
| 5,193,563 A | * 3/1993 | Melech | |
| 5,265,628 A | 11/1993 | Sage et al. | |
| 5,522,411 A | 6/1996 | Johnson | |
| 5,562,248 A | 10/1996 | Khalifka | ...................... 239/316 |
| 5,655,713 A | * 8/1997 | Gibney et al. | |
| 5,727,579 A | * 3/1998 | Chardack | |

FOREIGN PATENT DOCUMENTS

| | | | |
|---|---|---|---|
| DE | 9318479.4 | 2/1993 | |
| FR | 2659217 | 9/1991 | ............... 134/56 R |
| WO | WO 83/00654 | 3/1983 | ............. B08B/3/02 |

* cited by examiner

*Primary Examiner*—Frankie L. Stinson
(74) *Attorney, Agent, or Firm*—Bereskin & Parr

(57) ABSTRACT

An apparatus for disinfecting a user's hands has a spray chamber or an open spray zone with an opening for a user to insert his or her hands into the chamber. A supply of a disinfecting solution is provided, and preferably comprises a storage tank with a concentrated solution. This solution is mixed with an incoming freshwater supply, e.g. in a venturi valve, and supplied through spray nozzles into the chamber. A sensor detects the presence of a user's hands and automatically operates the spray nozzles for a predetermined time. The apparatus can also include a fan with its own timer, to provide a supply of drying air. Thus, a user can insert his or her hands, disinfect them with the disinfecting solution, remove the hands and dry them, without requiring any manual operation.

30 Claims, 12 Drawing Sheets

APPARATUS FOR AND METHOD OF DISINFECTING HANDS

RELATED APPLICATIONS

The following is a Continuation-in-Part Application to U.S. patent application Ser. No. 08/867,028, filed on Jun. 2, 1997 now abandoned.

FIELD OF THE INVENTION

This invention relates to a method and apparatus for disinfecting a user's hands, and more particularly is concerned with apparatus which enables disinfecting of hands, without requiring a user to manually operate or physically touch the equipment.

BACKGROUND OF THE INVENTION

There are many instances, in a variety of businesses and institutional situations, where it is desirable, or even essential, that a person have clean hands. For example, anyone handling food, in restaurants or other situations, should ensure their hands are well cleaned, before handling food. In a variety of medical and laboratory situations, it is necessary for personnel to clean their hands regularly, to ensure that an individual does not pick up a disease or infection and to prevent transmission of disease and infection.

In many cases, while facilities might be provided for cleaning or washing of hands, these are not completely effective. In many cases, this requires someone to seek out a washroom or the like, in order to wash or clean their hands. If washrooms and the like are not properly maintained, there can be problems with soap or cleaning solutions being available and/or towels to dry one's hands.

Devices have been proposed on the art. U.S. Pat. No. 5,265,628 (Sage et al) discloses an automated cleansing chamber. This discloses a relatively complex machine in which two separate cylinders are provided, for a user's two hands. The intention is that each hand would be inserted into a respective cylinder. The cylinders are rotated and provided an array of nozzles to wash the user's hands. A program is provided comprising purge, wash, dry, rinse and self-clean cycles. Mechanically, the system is complex, and includes numerous moving parts, which would be subject to wear and deterioration.

An alternative proposal is found in the Stevenson U.S. Pat. No. 2,814,081. This provides a circled rapid hand sanitizer. It provides a transparent, generally rectangular housing, which is intended for conspicuous display, so that patrons in the restaurants and the like can see that a server is sterilizing his or her hands, etc. It again provides two separate openings into the enclosure. To prevent spray and the like from being splashed, etc. out the enclosure, a flexible closure is retained by grommet mouldings for each opening. This means that the flexible closure rubs against the user's hands, possibly transferring bacteria and the like to or from the user's hands. A single spray nozzle is provided, directed at least partially towards the openings from the user's hands, which will aggravate the problem of spray accidentally passing out of the unit. Somewhat surprisingly, while a number of apertures are provided in the bottom of the casing, apparently to exhaust air from a blower, no provision is made for drainage of any excess liquid sprayed onto a user's hands.

Accordingly, it is desirable to provide a device that can be used for disinfecting or sanitizing a user's hands, which device should be simple, compact and readily installed at a variety of different locations. The present inventor has additionally realised that the present invention should ideally automatically provide a disinfecting solution, without requiring manual operation by the user.

For a disinfecting or sanitizing operation, the inventor has realized that it is not necessary to provide a large volume of liquid. Rather, it is only necessary to provide a small quantity of liquid. Additionally, much of the prior art fails to provide a design or device which will appeal to users or encourage them to use the device. Thus, many people are reluctant to insert their hands through any small opening into a closed chamber, since they are not sure exactly how the device will operate or how their hands will be treated.

The present inventor has also realized that, unlike much of the prior art, it is not necessary to have a user thoroughly wash his or her hands. Rather, what is required, is to have a user disinfect the hands. For this purpose, it is sufficient to have a user thoroughly coat his/her hands with a disinfecting solution and rub this solution into the hands. This then eliminates the need for any distinct rinsing or drying steps.

SUMMARY OF THE INVENTION

In accordance with a first aspect of the present invention, there is provided an apparatus for disinfecting a user's hands, the apparatus comprising:

a housing defining a spray zone, the spray zone being substantially open at the front thereof to enable a user to insert both hands and to manipulate both hands within the spray zone without contacting the housing, the housing including a collection portion for collecting excess spray from the spray zone;

a spray means comprising a plurality of spray nozzles mounted on the housing and directed rearwardly away from the front of the spray zone, for generating a spray of a liquid within the spray chamber and mounted on the drum;

a supply means for supplying a liquid to the spray means;

a valve means connected between the supply means and the spray means for controlling supply of the cleaning liquid;

a sensor means mounted on the spray chamber, for sensing the presence of a user's hands within the spray chamber; and a control circuit including a first timer and connected to the sensor means and the valve means, the control circuit being adapted to open the valve means to supply the liquid to the spray means when the sensor means detects the presence of a user's hands and maintaining the valve means open for a period determined by the first timer.

Preferably, the supply means comprises a storage tank for a concentrated solution and a first inlet for a water supply, and the valve means is then connected to both the first inlet and the storage tank and has an outlet connected to the spray means, the valve means, when open, mixing the concentrated solution and the water in a desired ratio, to form a dilute solution to form said liquid which is supplied to the spray means. The spray chamber preferably then includes an outlet for waste disinfecting solution, adapted to be connected to an external drain.

Advantageously, the valve means comprises a venturi valve.

The apparatus can further include a fan means for providing a flow of drying air. The fan is conveniently connected to and controlled by the control circuit and the control circuit then preferably includes a second timer for timing operation of the fan. The fan is provided mainly to encourage a user to rub the hands together, to promote even distribution of the liquid. In a preferred aspect of the invention only a small quantity of liquid is spraying, so that a full drying steps or cycle is not required.

More preferably, the control circuit includes a relay and the valve means includes an actuating solenoid. The first timer is then connected to the relay for actuation thereof, and the relay includes a first contact means connected to the solenoid for actuation thereof, to open the valve means, and to the second timer, to commence actuation thereof.

In a more preferred aspect of the present invention, the opening is provided at the front of the spray chamber and the spray means comprises a pair of spray nozzles mounted to the spray chamber below the opening and directed upwardly and rearwardly, and optionally a further spray nozzle mounted above the opening and directed downwardly and rearwardly.

The storage tank can be mounted either above or below the spray chamber. In a preferred embodiment, the storage tank is mounted above the spray chamber, so as to provide a compact unit which can be mounted on a counter surface or the like. The supply means preferably includes a filling funnel mounted above the spray chamber and connecting to the storage tank. A vent, to vent air from the storage tank during filling, can either be connected to the exterior or to the spray chamber.

Another aspect of the present invention provides a disinfecting solution and the storage tank is preferably filled with this solution, the disinfecting solution comprising:

1.6–2% N-alkyl dimethyl benzyl ammonium chloride;
1.6–2% didecyl dimethyl ammonium chloride;
0.2–0.4% lauramine oxide;
0.2–0.6% tetrasodium salt of EDTA;
4% glycerin; and water, the amount of water forming the balance of the composition.

BRIEF DESCRIPTION OF THE DRAWINGS

For a better understanding of the invention, and to show more clearly how it may be carried into effect, reference will now be made, by way of example, to the accompanying drawings, in which.

DETAILED DESCRIPTION OF THE PREFERRED EMBODIMENT

Figure 1:
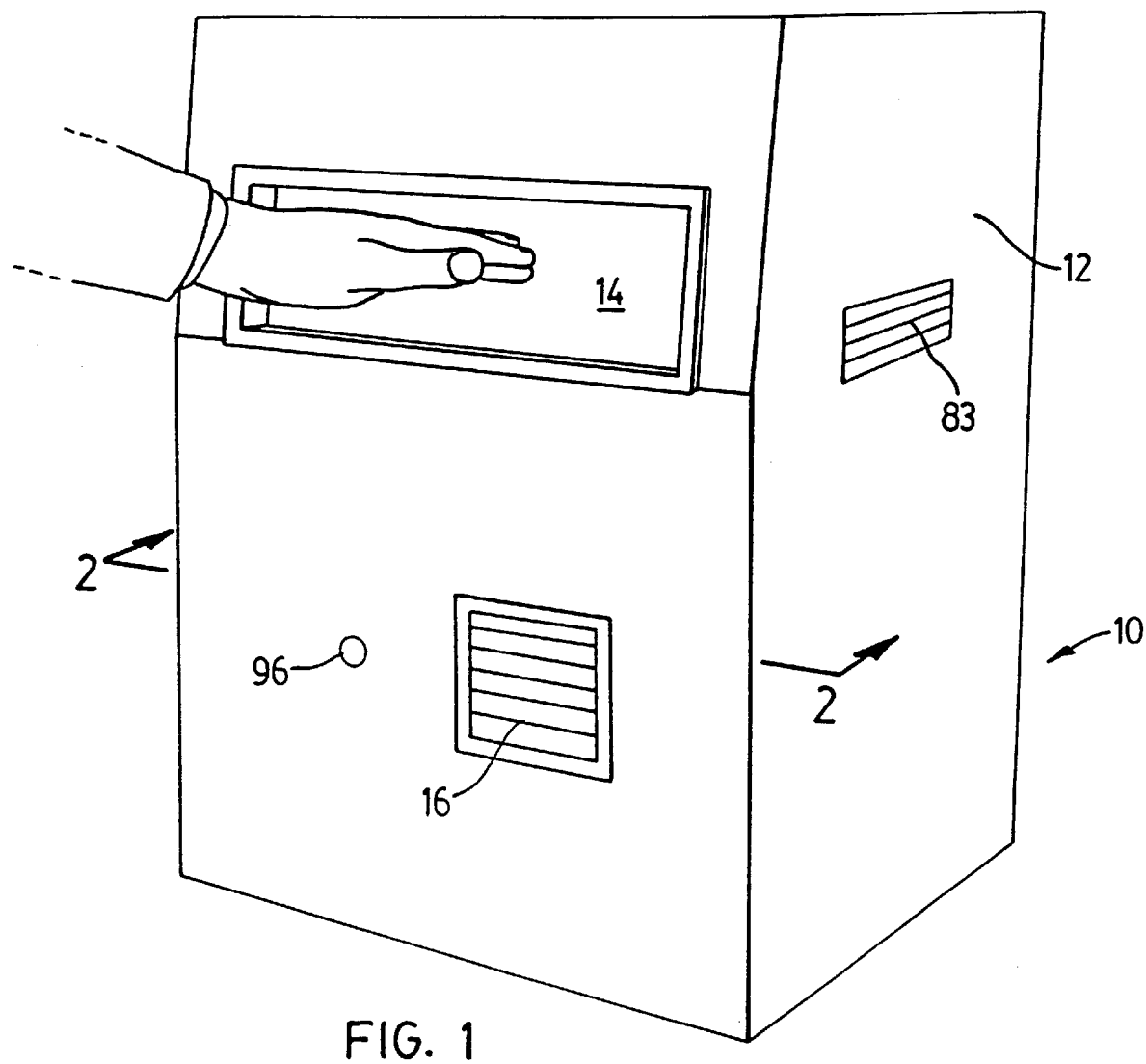
FIG. 1 is a perspective view of an apparatus in accordance with the present invention.

A first embodiment of an apparatus in accordance with the present invention is indicated generally by the reference 10. The apparatus 10 has an external casing 12, which can be formed from sheet metal or the like in known manner. As shown in FIG. 1, this casing 12 includes an opening 14 for a user's hands, as detailed below, and an outlet vent 16 for a fan.

Figure 5:
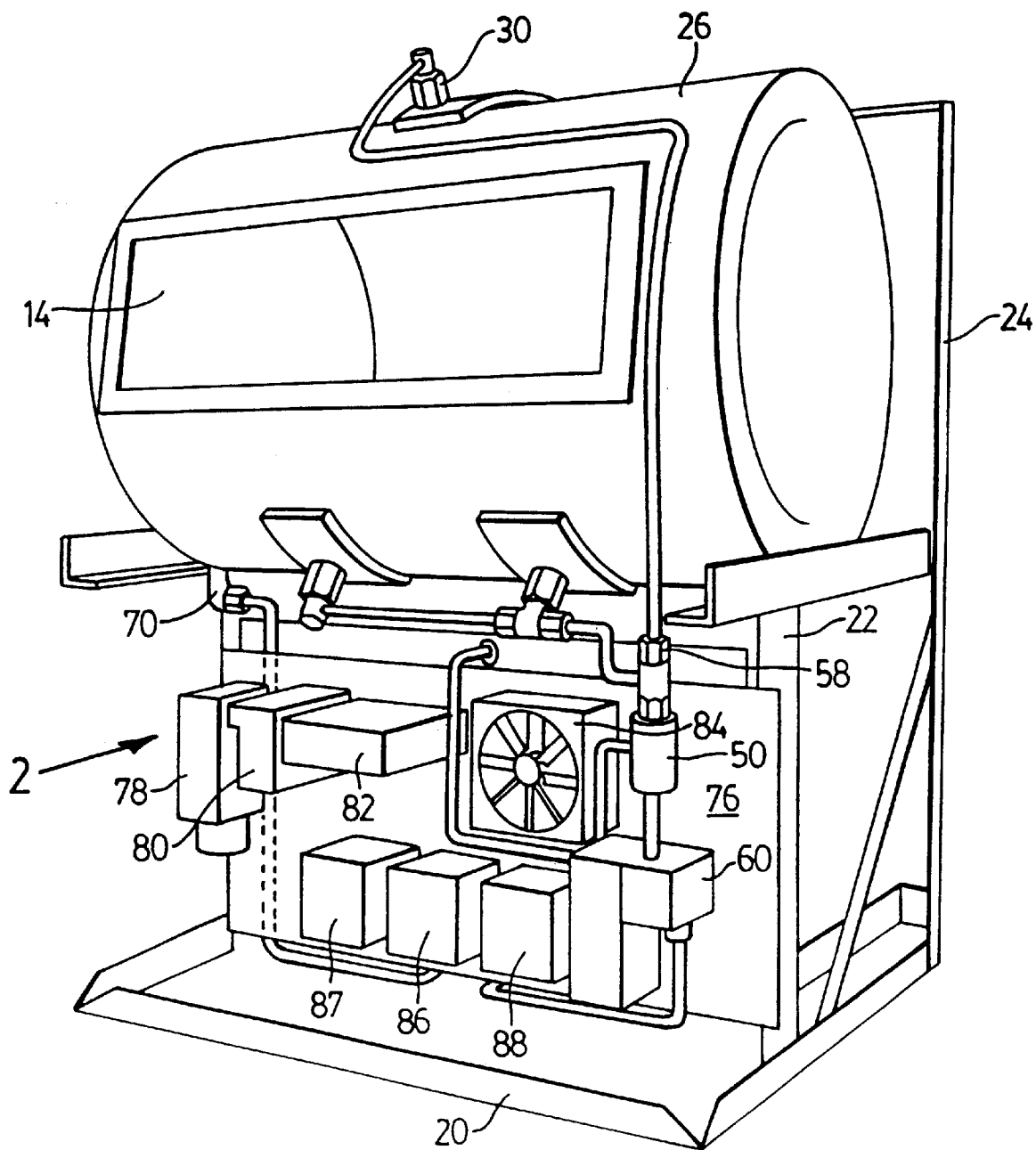
FIG. 5 is a perspective view, similar to FIG. 1, showing an outer casing removed.

Referring to FIG. 5, with the casing 12 removed, the apparatus 10 shows a base 20, with a support framework 22 extending upwardly from the base 20. A rear wall 24 extends up from the base 20, and forms part of the casing 12.

Figure 4:
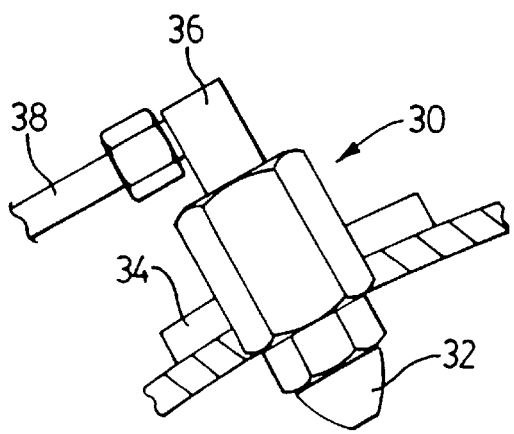
FIG. 4 is a detailed, enlarged view of a single spray nozzle.
Figure 2:
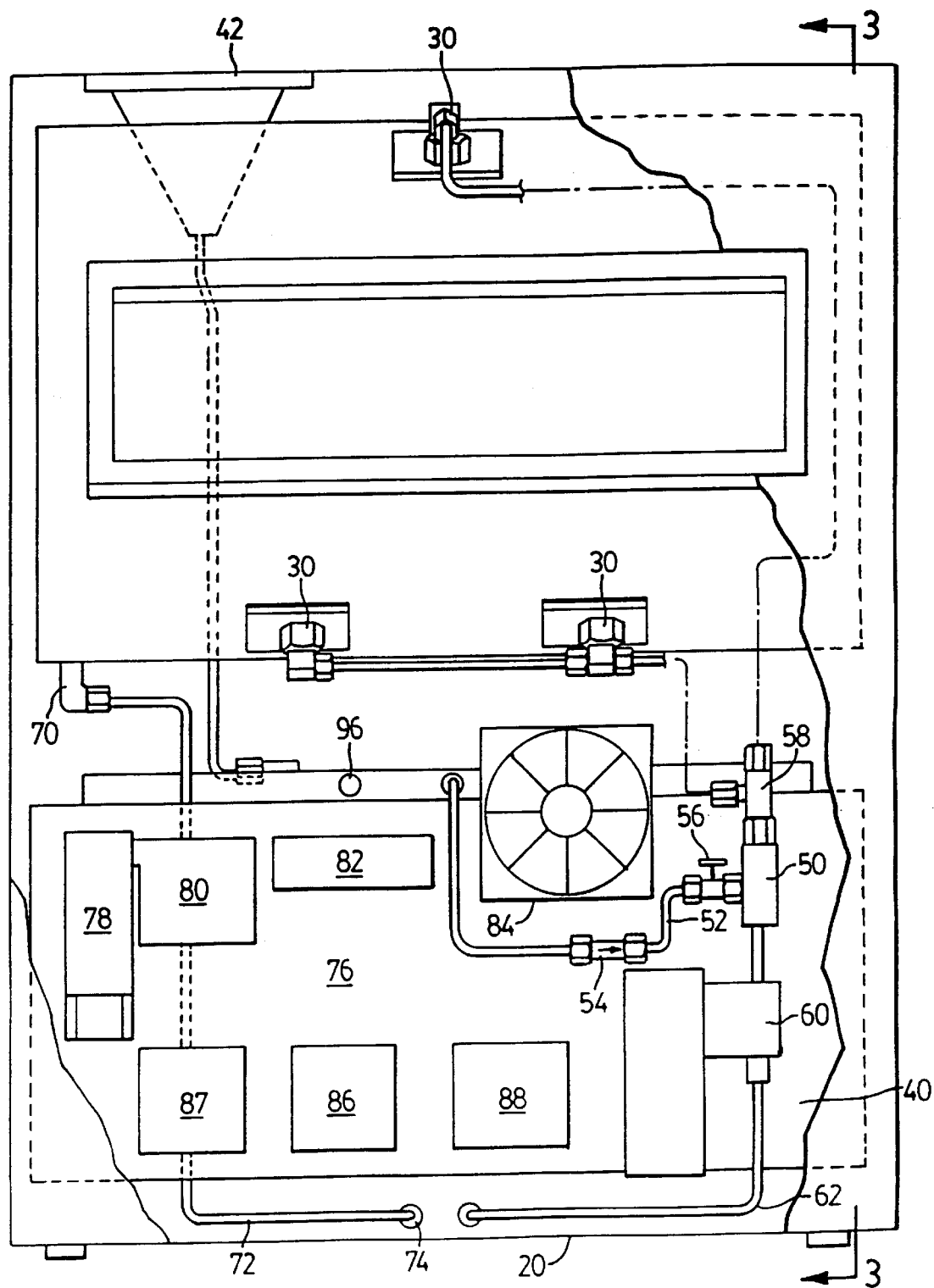
FIG. 2 is a sectional view looking in the direction of arrows 2—2 of FIG. 1.
Figure 3:
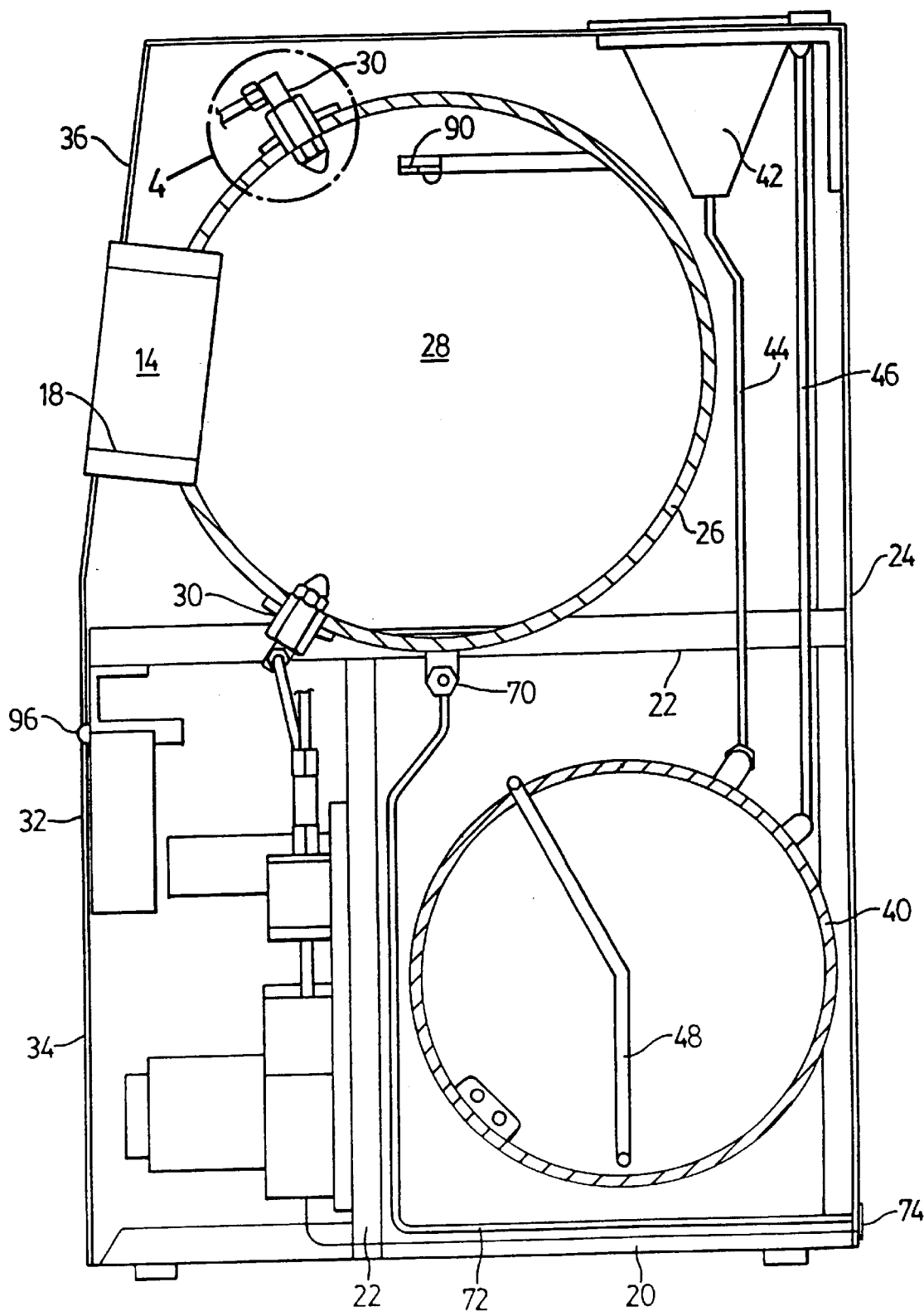
FIG. 3 is a sectional view looking in the direction of arrows 3—3 of FIG. 2.

Mounted on top of the support framework 22 is a drum 26 defining a cylindrical spray chamber 28. The opening 14 is rectangular and is inclined downwardly into the cylindrical spray chamber 28 as shown. As most clearly shown in FIG. 3, the opening 14 is defined by a generally rectangular tubular member 18, effectively extending through the outer casing 12 and into the spray chamber 28. As shown in FIGS. 2 and 3, three spray nozzles 30 are mounted in the drum 26. Details of the nozzles 30 are shown in FIG. 4. Each nozzle 30 comprises an atomizing fog nozzle producing a divergent spray. The preferred spray nozzle is a Lennox humidifier nozzle #21060 with a #54G49 holder supplied by LENNOX. This provides a 90° wide hollow cone spray at a flow rate of 3.00 gallons per hour. The actual atomizing nozzle is indicated at 32 and is secured to a mounting bracket 34, which clamped, secured by adhesive or otherwise attached to the drum 26. An angled compression fitting 36 provides a connection to flexible P.V.C. tubing 38, the tubing 38, together with other standard fittings connecting the nozzles 30 together.

Below the drum 26, there is a storage tank 40 for a concentrated disinfecting solution, details of which are given below. The storage tank 40 is provided with a screened, generally conical refilling funnel 42 connected by tubing 44 to the top of the tank 40. A back pressure vent tube 46 (see FIG. 3) is provided.

A filtered suction pickup 48 extends from near the bottom of the tank 40 out through the top surface of the tank 40, and as shown in FIG. 2, to a venturi valve 50. This connection is made by further tubing 52 and a non-return valve 54. A valve 56 is provided to enable the flow rate through the venturi valve 50 to be adjusted. The outlet of the venturi valve 50 is connected to a union 58, providing a connection to the spray nozzles 30.

The inlet of the venturi valve 50 is connected by a solenoid valve 60, including an actuating solenoid, to an inlet 62 providing a connection to a conventional freshwater source, i.e. to a water supply within a building.

The venturi valve 50 is preferably a single stage injector, supplied by DEMA Engineering Company of St. Louis, Mo., U.S.A. It serves to dilute the concentrated disinfecting solution to a desired ratio with the water, to form a dilute solution.

Figure 6:
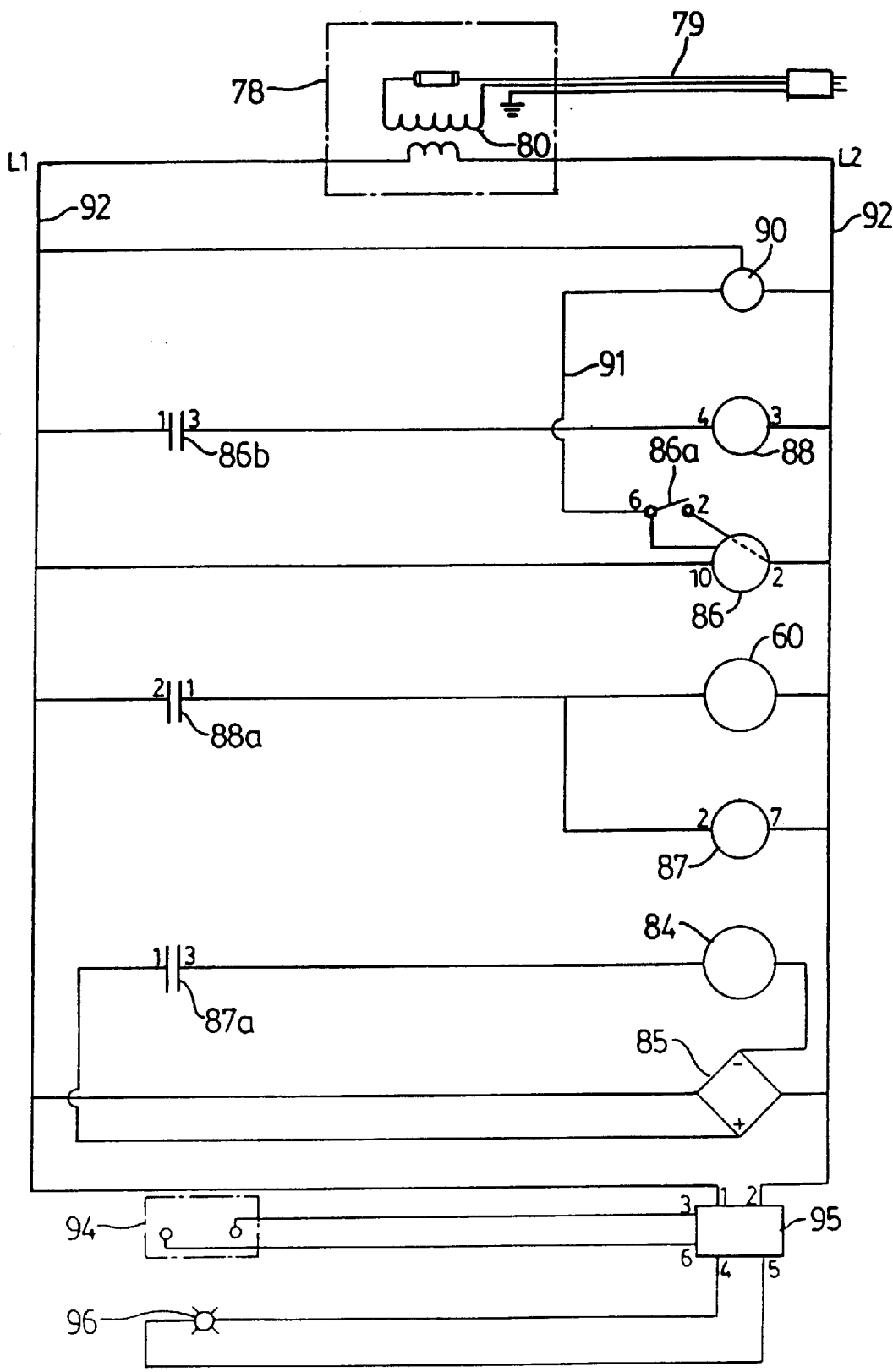
FIG. 6 is a schematic of an electrical control circuit.

For waste water disinfecting solution, an outlet 70 is provided in the bottom of the drum 26. This outlet 70 is connected by tubing 72 to an outlet 74, which can be connected to conventional drains within a building. At the front of the apparatus 10, various electrical control elements are arranged on a panel 76. The electrical interconnection of these various elements is shown in FIG. 6. A junction box 78 is provided with an input lead 79 (FIG. 6), for connection with a conventional electricity supply, for example, 120 volts AC in North America. The junction box 78 is connected to a transformer 80 which converts the input supply to a 24 volt AC supply for powering the other components, as indicated in FIG. 6. The junction box 78 and transformer 80 are weather proof and designed to withstand water spillage.

Mounted on the right hand side of the transformer 80, as shown in FIG. 2, is a housing 82 for various low level electronics, and beside this is a fan 84. 2"×4" louvered vents 83 are provided for the incoming air to the fan 84.

Along the bottom of the panel 76, there is a first, multifunctional timer 86 for the spray nozzles and a second timer 87 for the fan, as detailed below. Beside the timers 86, 87, there is a relay 88. Also forming part of the electronic circuitry is a photoelectric proximity sensor 90, shown in FIG. 3. Preferably, this is Model No. E65-SMSD200-HL supplied by, Cutler-Hammer Eaton of Cleveland, Ohio, U.S.A.

Turning to FIG. 6, as shown, the transformer 80, effectively included in the enclosure 78 of the junction box is provided with the input 79 for connection to a conventional 120 VAC supply. This is transformed down to 24 volts AC and connected to a pair of supply lines 92.

As shown, the proximity sensor 90 is connected between the lines 92 and has an output 91, connected to the first timer 86. A contact pair 86a is an internal contact pair of the timer and serves to initiate operation of the timer 86. The timer 86 controls a pair of contacts 86b, which when closed actuate the relay 88. The relay 88 in turn closes a pair of contacts 88a, so as to actuate the solenoid valve 60. Simultaneously, the closure of the contacts 88a activates the second timer 87.

The second timer 87 closes a pair of contacts 87a, to provide power to the fan 84. As shown, for the fan 84, a bridge rectifier 85 is provided between the supply lines 92, to provide a DC supply for the fan 84.

Additionally, to monitor the level of liquid in the storage tank 40, a probe 94 is provided. The probe 94 is connected to a level sensor 95, which is also connected to a lower level warning light 96 which is provided through the front of the casing 12.

Accordingly, in use, the apparatus is installed and connected up to conventional electrical and freshwater supplies. The storage tank 40 is filled with a suitable concentrated disinfecting solution through the funnel 42. In accordance with the present invention, a preferred disinfecting formulation comprises:

1.6–2% N-alkyl dimethyl benzyl ammonium chloride;
1.6–2% didecyl dimethyl ammonium chloride;
0.2–0.4% lauramine oxide;
0.2–0.6% tetrasodium salt of EDTA;
4% glycerin; and water, the amount of water forming the balance of the composition.

When a user wishes to disinfect his/her hands, he or she simply inserts the hands through the opening 14. The presence of the hands is detected by the proximity sensor 90. This activates the first timer 86, which in turn actuates the relay 88. The relay 88 opens the solenoid valve 60, permitting fresh water to flow through to the venturi valve 50. In the venturi valve 50, the low pressure entrains disinfecting solution from the tank 40 into the freshwater flow, to provide a desired dilution of the cleaning solution in the range 80:1 to 200:1. The disinfecting solution is then sprayed from the nozzles 30 and, in known manner, the user can rub his or her hands together and ensure they are adequately covered with the solution. The spraying operation is timed for a period set by the timer 86. The sloping of the opening 14 ensures that any drops of solution falling on it are directed back in the chamber 28.

Unlike many other proposal in this field, which rely on spraying relatively large quantities of a liquid or cleaning solution to effect it through washing action, the present invention is intended primarily to provide a disinfecting or sanitizing function. As such, it is recognized that only a relatively small amount of liquid needs to be sprayed. To this end, it is preferred for the spray nozzles to provide a combined spraying rate in the range of 2.5 to 3.2 GPH. Then, the spray nozzles can be actuated for a time in the range of 0.2 to 1.2 sec. Put another way, the total amount of liquid sprayed is preferably in the range of 3 to 5 cc. The most preferred operative conditions are two spray nozzles each operating at 3.00 gallons per hour providing a relatively fine mist or fog, with the spray nozzles operated at 0.5 seconds. This gives a total volume sprayed of 3.0 cc.

Then, it has been found that approximately 70% of the liquid sprayed coats the skin of the user's hands, with only a small or minor portion of the liquid being lost to waste. When the user removes his hands from the device, the fan 84, as detailed below is actuated. However, in view of the relatively small volume of liquid that is deposited on the hands, no true drying action is required. Rather, the fan is provided more to encourage users to rub their hands together, to ensure even coverage of the hands with the liquid. It can be further noted that since no true drying action is required, the whole cycle takes a matter of a few seconds, which encourages users to use the device. It is not time-consuming, and does not require any separate true drying step, as in an apparatus that provides a full washing action.

When the solenoid 60 is actuated, as shown in FIG. 6, the second timer 87 is also actuated. This timer 87 can then immediately, or after a set delay, actuate the fan 84. In any event, the timer 87 sets the fan 84 to run for a second period of time after the timer 86 is turned off and the dispensing of the disinfecting solution ended.

The fan 84 produces a flow of air, discharging out from the outlet vent 16. Thus, after a user has disinfected his or her hands, their hands can be placed in front of a vent and rubbed together. If desired, a heater can be provided in addition to the fan 84.

The fan and flow of air do not here provide a true drying action. Rather, it is provided simply to encourage a user to rub the hands together to spread the solution uniformly over the hands.

At the end of the second time period, the timer 87 shuts off the fan 84, and the apparatus can then remain dormant and ready for another user.

The casing 12 can be formed in any known manner. Here, the casing 12 has generally rectangular top and bottom surfaces and includes the rectangular rear wall 24. At the front, the casing 12 has a front wall 32, with lower and upper portions 34, 36 (FIG. 3). The lower portion 34 is generally vertical and the upper portion 36 is inclined backwards slightly, with the opening 14 perpendicular to the upper portion 36. The sides of the casing 12 are then correspondingly shaped.

Figure 7:
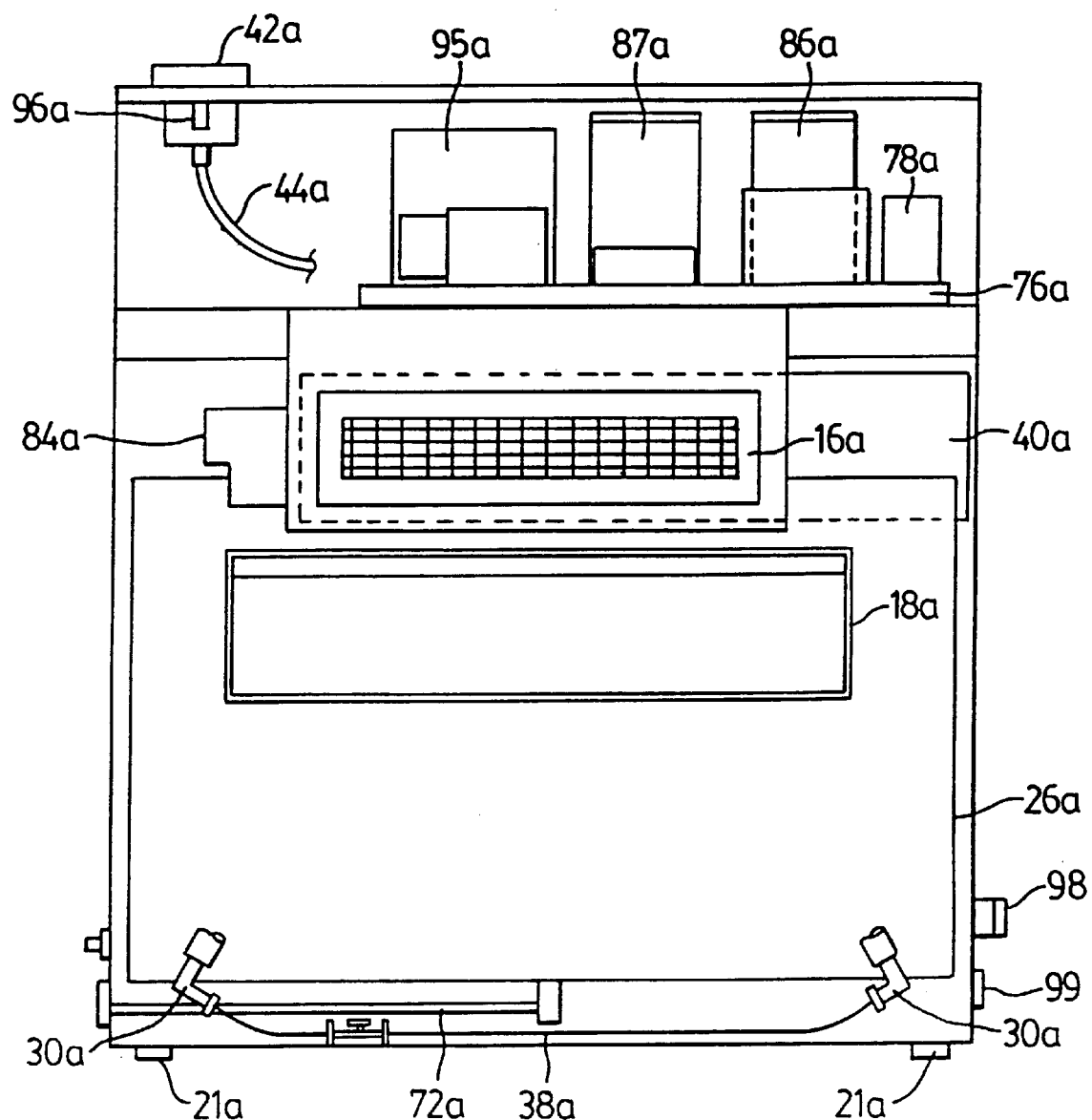
FIGS. 7 and 8 show views similar to FIGS. 2 and 3 of a second embodiment of an apparatus in accordance with the present invention.
Figure 8:
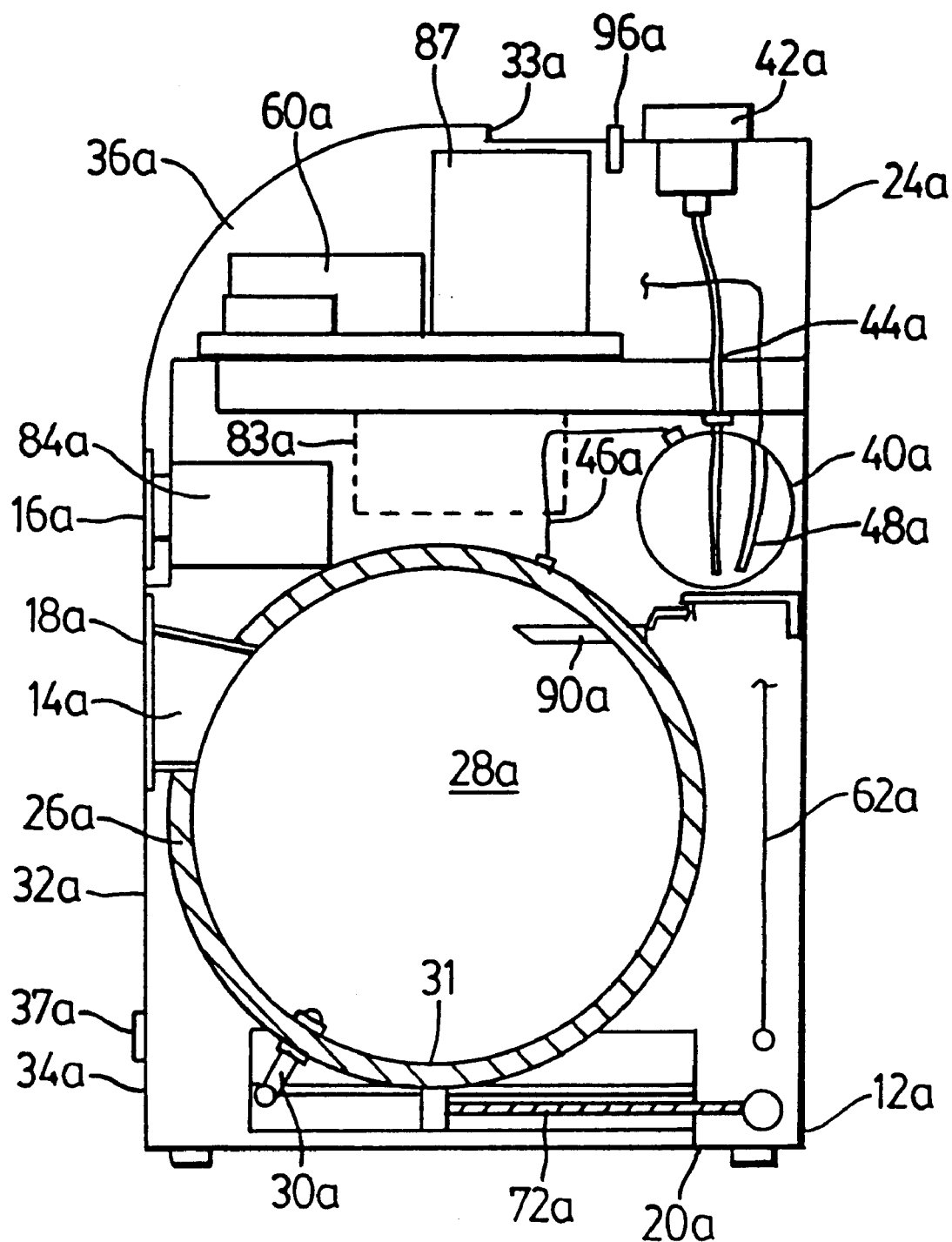
Figure 9A:
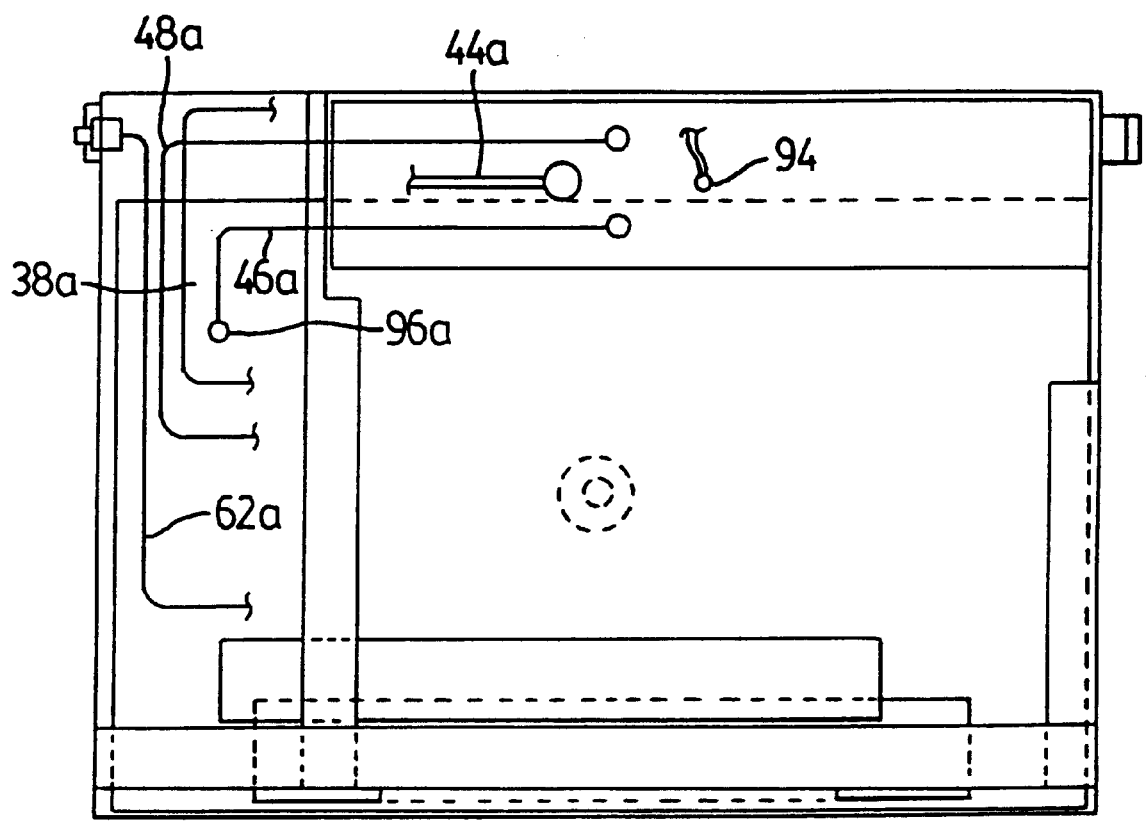
FIG. 9a is a sectional view in a horizontal plane of the second embodiment.

In FIGS. 7–9, a second embodiment is shown and denoted by the reference 100. Elements common to the first embodiment are given the same reference numeral as in the first embodiment, but with the suffix a. For brevity, a detailed description of similar or common components is not repeated, and it is to be understood that the individual components function as in the first embodiment.

The second embodiment of the apparatus 100 provides a more compact unit intended for mounting on a counter, table, wall or the like. As such, in many institutional, business and other settings, it should be easy to find a suitable surface for mounting the unit, and it then occupies little space.

The principal difference in the second embodiment is that the drum is now located below the storage tank. This is because the unit is intended for mounting on an elevated surface. For this purpose, the drum 26a has an external diameter of 10 inches. The drum is centered at 6¼ inches above the base 20a of the device. Here, rubber bumper pads 21a are provided. Consequently, the opening 14a is much closer to the base 20a than in the first embodiment.

The arrangement of the spray nozzles is modified as compared to the first embodiment. A single pair of nozzles 30a are provided. In FIG. 7, these are inclined at an angle of 60° towards the centre of the chamber, as viewed from the front. Similarly, as shown in FIG. 8, the nozzles 30a are also inclined at 60° to the horizontal, so as to be directed rearwardly.

The opening 14a is now tapered, and is provided above the centre line of the drum 26a, as best shown in FIG. 8. At the bottom of the drum 26a, there is a drain screen 31 provided above the outlet connected to the outlet tube 72a. The back pressure vent 46a, instead of being connected to atmosphere, is now connected to the spray chamber, as shown.

The arrangement of the fan has now been altered. The fan 84a has the actual fan or drive motor provided on one side, as shown in FIG. 7. An elongate grill or outlet vent 16a is provided. Again, this is merely to encourage a rubbing or massaging action, and not to provide a true drying function.

Turning to the arrangement of the control circuitry, similar components are provided as for the first embodiment and these operate similarly. However, the physical layout of their components has been varied.

Figure 9B:
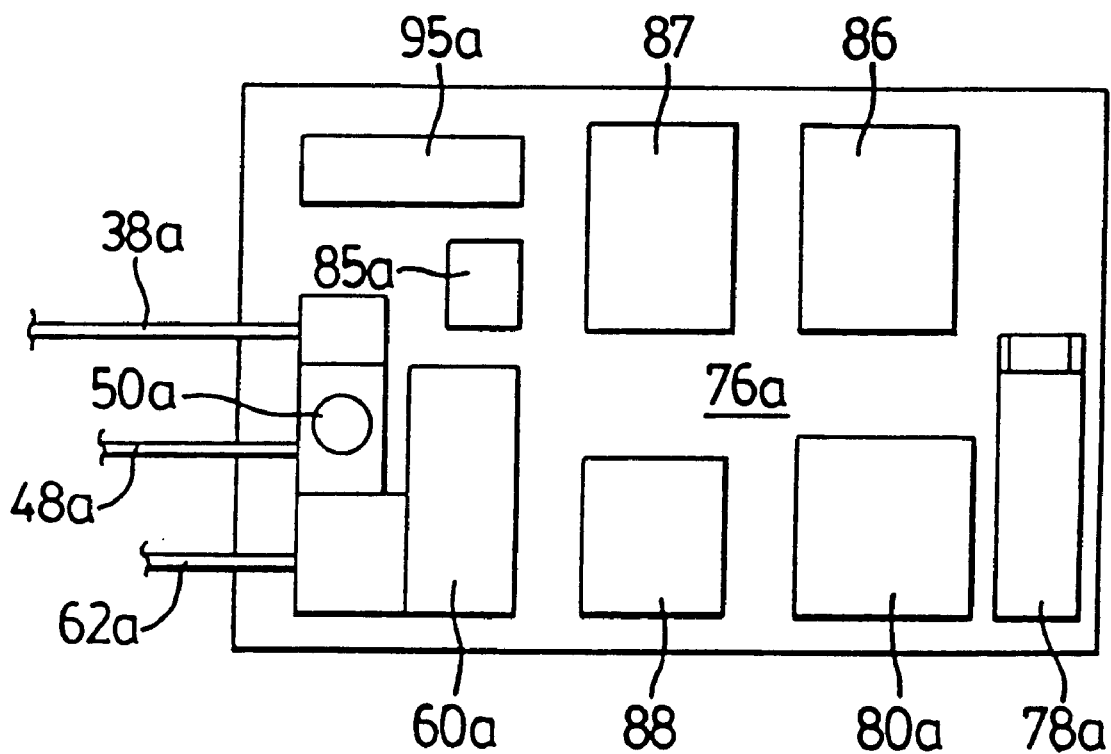
FIG. 9b is a view similar to FIG. 9a, showing details of a panel with electrical components.

Thus, the panel 76a is now horizontal. The arrangement of the solenoid valve 60a and the venturi valve 50a are shown in FIG. 9b. The non-return valve 54 and the valve 56 setting the flow rate would be retained, and the outlet of the venturi valve 50a is connected to tubing 38a and then through to the nozzles 30a.

The overall profile of the front panel 32a is varied. It has a planar lower portion 34a and a rounded upper portion 36a. At its upper edge, as indicated at 33a, there is a hinge or the like permitting the front cover to be detached. A cam lock 37a at the bottom enables the front cover to be released at the bottom and then pivoted upwards. The hinge arrangement 33a can comprise a tongue and groove arrangement formed between folded ends of the panel sheets, permitting the front panel 32a to be removed, for servicing, maintenance etc. On the right hand side as indicated at 98, a NEMA 4 fuse holder can be provided and 99 indicates a grommet for an input power supply cable.

The tubing for the different connections can be sized for the intended use. In this preferred embodiment, the connection tube 44a for filing the storage tank and the drain tube 72a are both ½ inch vinyl tubing. The other tubing, the connection tubing 38a to the nozzles, the back pressure vent tubing 46a, the filtered suction pick-up tubing 48a and the water inlet connection tubing 62a are all ¼ inch P.V.C. tube.

Figure 10A:
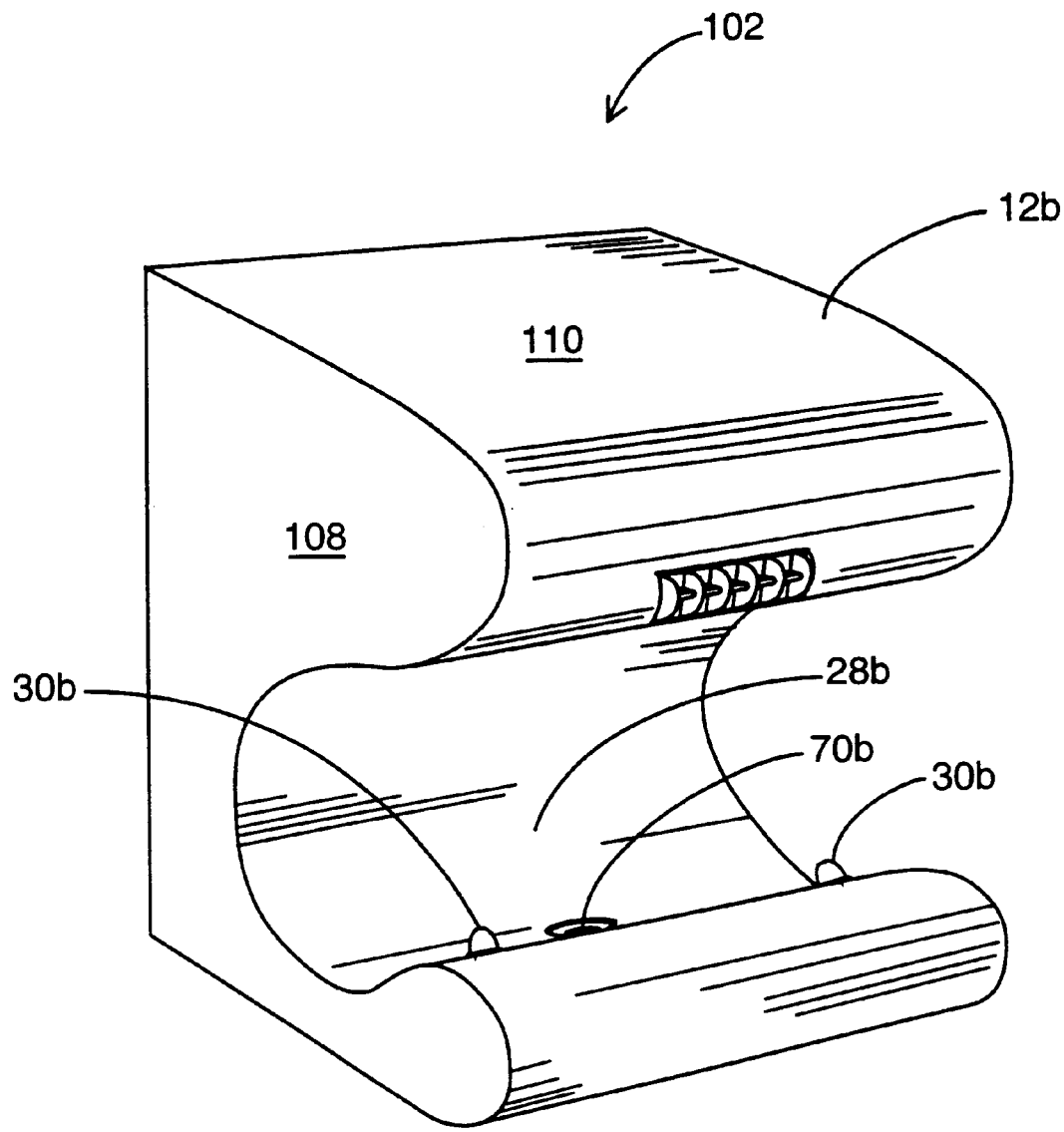
FIG. 10a is a front, perspective view of a third embodiment of an apparatus in accordance with the present invention.
Figure 10B:
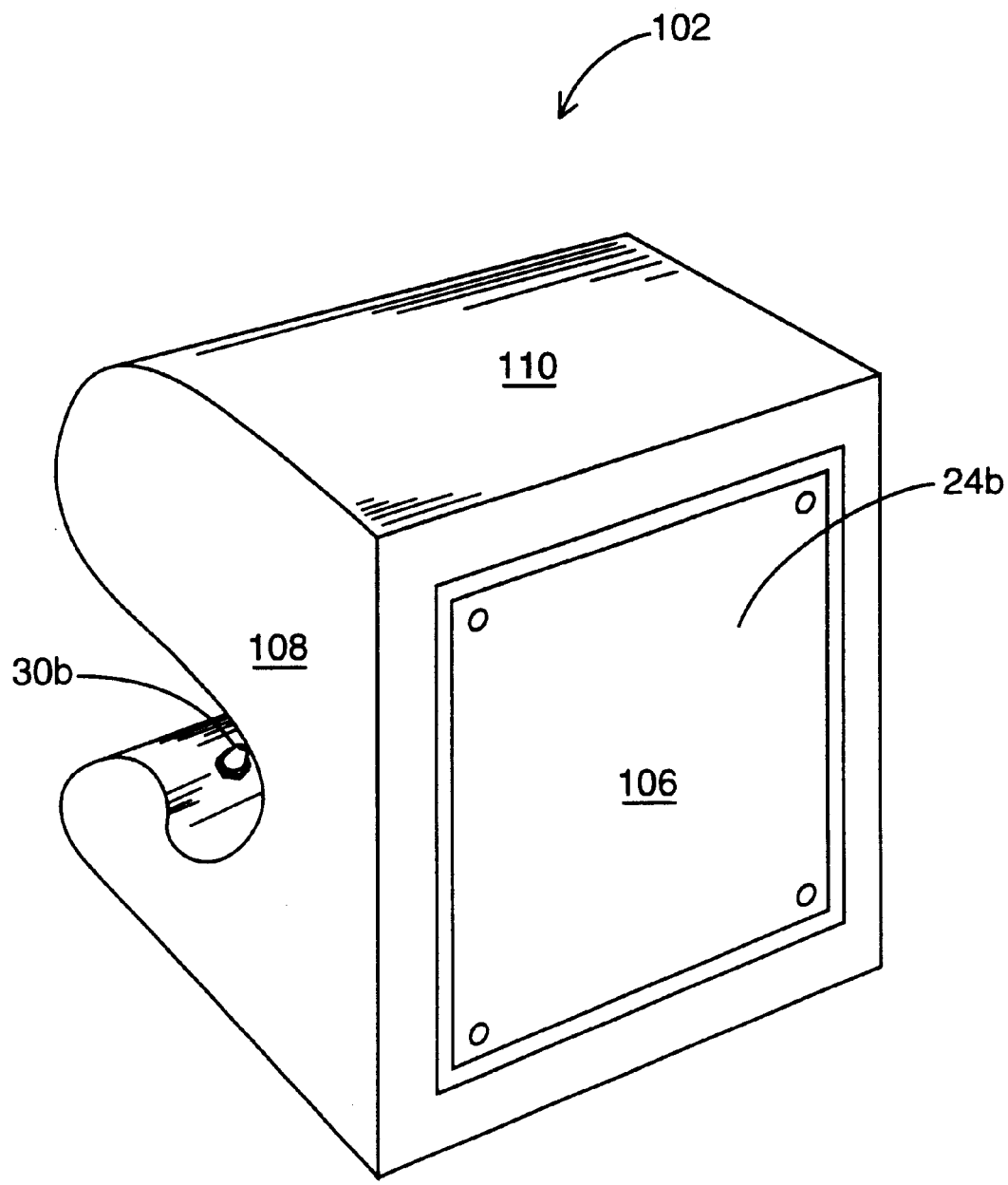
FIG. 10b is a rear perspective view of the third embodiment of the apparatus.
Figure 10C:
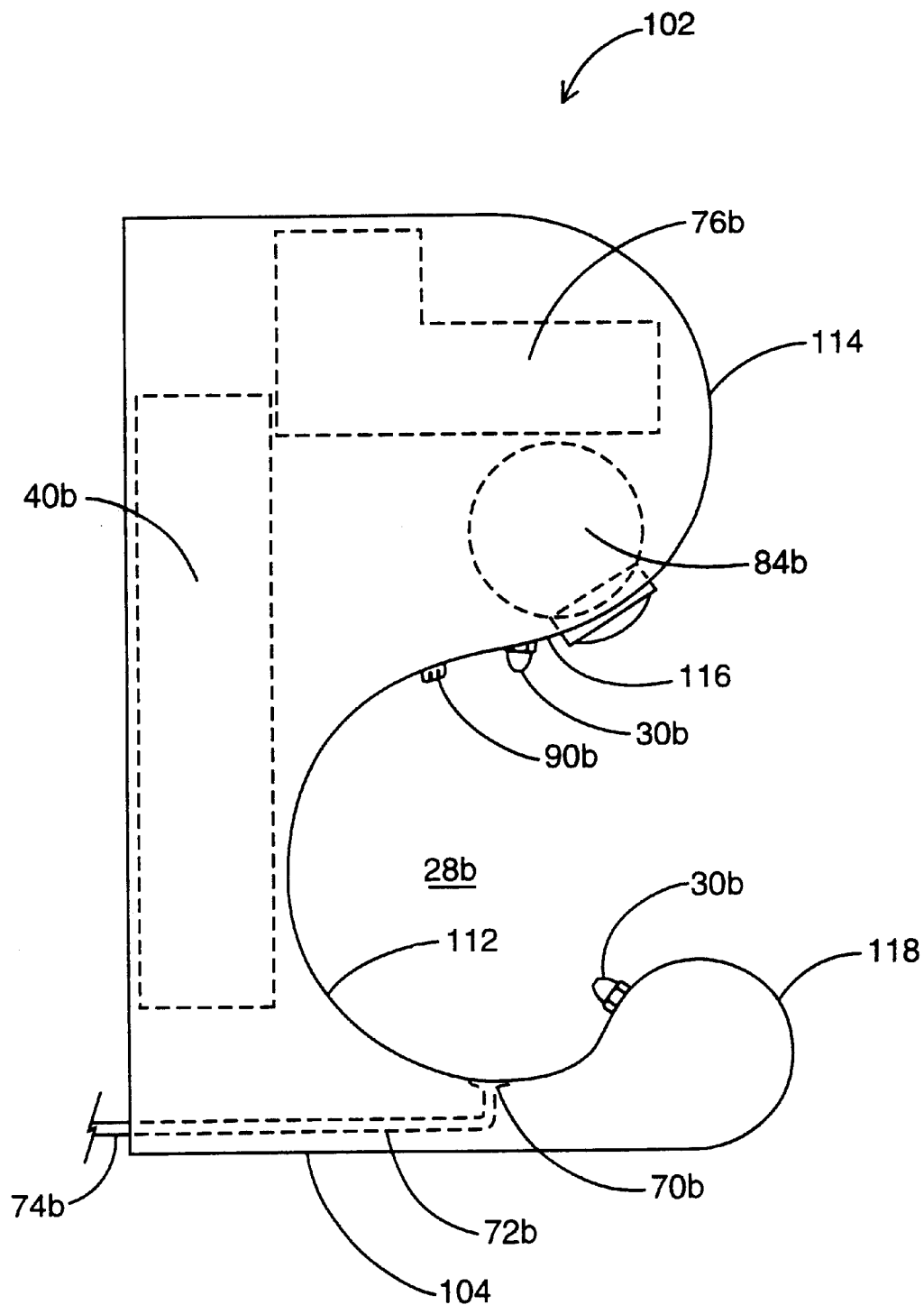
FIG. 10c is a side view of the third embodiment of the apparatus.

Referring now FIGS. 10a, 10b and 10c, a description of a third and preferred embodiment will now be given. Again, elements common to the first and second embodiments are given the same reference numeral, but here are denoted with a suffix b. Also, as for the second embodiment, a detailed description of components common to at least one of the first and second embodiments, is not repeated, and it is to be understood that many components would be common with those in the first and second embodiments and would function in the same manner. The principal difference in this third embodiment is the overall configuration of the exterior of the housing and the zone or chamber for spraying a solution onto a user's hands, and just these features are described in detail below.

This third embodiment is designated by the reference 102. It is intended as a compact unit, for mounting either on a table or other suitable horizontal support surface or on a wall.

As such, the second embodiment 102 has a planar base 104 and a rear wall 24b consisting largely of a removable rear panel 106. The panel 106 provides access to the interior working components in known manner, for servicing and repair.

The housing 12b includes planar side walls 108 and a planar top surface 110. The peripheries of the side walls 108 are determined by the shape of the other surfaces or panels.

Unlike the previous embodiments where a distinct spray chamber was provided and was defined by a separate drum or the like, no distinct fully enclosed spray chamber is provided, rather, there is a spraying zone here designated at 28b. The spraying zone 28b is defined primarily by an inner, concavely-shaped wall having a radius of 4½ inches as viewed in the cross-section of FIG. 10c, this concavely-shaped wall portion being indicated at 112. Above the wall portion 112, there is an upper convexly-shaped wall 114, also having a radius of 4½ (again as in FIG. 10c), extending from the top wall or panel 110 and continuing smoothly into the concavely-shaped wall 112. The centers of a curvature of the two walls 112, 114 are spaced apart by 9.45 inches, i.e. by slightly more than the radius. A transition portion 116 between the two curved walls 112, 114 is generally planar.

At the bottom of the housing 12b, there is a front or lower convexly-shaped wall 118 having a radius of 2 inches (again, as in FIG. 10c) and centered 2 inches above the base 104, so as to continue smoothly into the base. The wall 118 extends through approximately 220 degrees and continues smoothly into the concavely-shaped wall 112.

Corresponding to the previous embodiments, a drain outlet 70b is provided at the lower-most portion of the wall 112, and is connected by tubing 72b to a drain outlet 74b. To ensure that excess liquid is contained by the wall 112 and does not flow off either end, either vertically upwardly extending lips can be provided or the center of the lower-most portion of the wall 112, i.e. around the drain outlet 70b, can be dished downwards. If lips are provided, these need be provided just to the lower-most portion of the wall 112, somewhat as extensions of the side wall 108.

The arrangement of spray nozzles again follows that of the earlier embodiments. Here, there are two lower spray nozzles 30b mounted to the forward convexly-shaped wall 118, these spray nozzles 30b being directed at an angle of 45 degrees to the horizontal, as viewed in FIG. 10c, and also directed inwardly. An upper spray nozzle 30b is mounted to the transition portion 116, and is directed primarily downwardly but slightly rearwardly. It can be noted that all the spray nozzles can be arranged so as to be directed primarily to the centered curvature of the concavely-shaped wall 112.

The other elements necessary for operation of this third embodiment would follow the previous embodiments, and are shown merely schematically. First, a blower is indicated at 84b, and would be directed forwardly and downwardly. As before, the blower 84b is intended mainly to encourage users to rub their hands together and obtain uniform coverage of a disinfecting solution. The amount of solution sprayed will be so small that no true drying action should be required.

Electronic controls are indicated at 76b. The storage tank stores the concentrated solution and is indicated at 40b, and as shown could be a generally rectangular parallelepiped.

In use, this third embodiment has the advantage that it is much more open, so as to encourage users to insert their hands. At the same time, it provides sufficient enclosure to contain spray and to collect and drain off any excess spray as only a fine mist of spray is used, in a small quantity, the problem of excess spray being splashed externally of the device should not be too great.

A user can insert his or her hands either directly from the front or indeed partially from the side. The relatively large open area enables a user to freely manipulate both hands and to rub the hands together, if desired, to obtain uniform coverage of the disinfecting solution. All of this can be accomplished without necessarily contacting the device or apparatus itself, thereby eliminating the problem of cross-contamination from one user to another.

It will be understood that the lower-most portion of the concavely-shaped wall 112 and at least part of the lower convexly-shaped wall 118, together with lips at either side, as provided, or a dish-shape, provide a trough-shaped collection portion for collecting excess spray. As noted, this excess spray is then drained off through the drain 70b.

The shape provided by the convex-shaped wall 114 provides an upper portion above the spray zone 28. Correspondingly, the shape provided by the lower portion of the concavely-shaped wall 112, together with the convexly-shaped wall 118 provides a lower portion defining the bottom of the spray chamber 28b. This lower portion is also considered to define a trough-shaped collection portion for collecting excess spray. The collection portion extends transversely and has ends at the two sides 108 of this embodiment.

It will be appreciated that while preferred embodiments of the present invention has been described, numerous variations are possible within the scope and spirit of the present invention.

What is claimed is:

1. An apparatus for disinfecting a user's hands, the apparatus comprising:
   a housing defining a spray zone, the spray zone being substantially open at the front thereof to enable a user to insert both hands and to manipulate both hands within the spray zone without contacting the housing, the housing including a collection portion for collecting excess spray from the spray zone;
   a spray means comprising a plurality of spray nozzles mounted on the housing and directed rearwardly away from the front of the spray zone, for generating a spray of a liquid within the spray chamber and mounted on the drum;
   a supply means for supplying a liquid to the spray means;
   a valve means connected between the supply means and the spray means for controlling supply of the cleaning liquid;
   a sensor means mounted on the spray chamber, for sensing the presence of a user's hands within the spray chamber; and
   a control circuit including a first timer and connected to the sensor means and the valve means, the control circuit being adapted to open the valve means to supply the liquid to the spray means when the sensor means detects the presence of a user's hands and maintaining the valve means open for a period determined by the first timer wherein the spray means is dimensioned and the first timer sets said period such that the total volume of liquid sprayed onto a user's hands is in the range of 3 to 5 cc.

2. An apparatus as claimed in claim 1, wherein the supply means comprises a storage tank for a concentrated solution and a first inlet for a water supply, and the valve means is connected to both the first inlet and the storage tank and has an outlet connected to the spray means, the valve means, when open, mixing the concentrated solution and the water in a desired ratio, to form a dilute solution to form said liquid which is supplied to the spray means.

3. An apparatus as claimed in claim 2, wherein the spray chamber includes an outlet for waste liquid, adapted to be connected to an external drain.

4. An apparatus as claimed in claim 3, wherein the valve means comprises a venturi valve.

5. An apparatus as claimed in claim 3, wherein the spray nozzles are, together, adapted to spray liquid at a rate in the range of 2.5 to 3.2 GPH, whereby the largest portion of the liquid sprayed remains on a user's hands and only a minor portion is discharged through the outlet.

6. An apparatus as claimed in claim 3, which includes a fan means for providing a flow of drying air, to encourage a user to rub the hands together to distribute the liquid over the hands.

7. An apparatus as claimed in claim 6, wherein the fan is connected to and controlled by the control circuit and the control circuit includes a second timer for timing operation of the fan.

8. An apparatus as claimed in claim 7, wherein the control circuit includes a relay and the valve means includes an actuating solenoid, wherein the first timer is connected to the first relay for actuation thereof, and the first relay includes a first contact means connected to the solenoid for actuation thereof, to open the valve means, and to the second timer, to commence actuation thereof.

9. An apparatus as claimed in claim 8, which includes a level sensor on the storage tank, wherein the level sensor is connected to the control circuit and the control circuit includes an indication means, for providing an indication when the level of concentrated solution in the storage tank falls below a predetermined level.

10. An apparatus as claimed in claim 3, wherein the spray means comprises a pair of spray nozzles mounted on the spray chamber below the opening and directed upwardly and rearwardly.

11. An apparatus as claimed in claim 10, wherein the storage tank is mounted below the spray chamber and the supply means includes a filling funnel mounted above the spray chamber and connecting to the storage tank and a vent to vent air from the storage tank during filling.

12. An apparatus as claimed in claim 11, wherein the valve means comprises a venturi valve and wherein the storage tank includes a filtered suction pickup extending from a position adjacent the bottom of the storage tank to the venturi valve.

13. An apparatus as claimed in claim 12, which includes a framework for supporting the spray chamber and the storage tank and an external casing surrounding the storage tank and the spray chamber, with the opening for the spray chamber extending through the casing into the spray chamber, wherein the apparatus is adapted for mounting on an elevated surface and the storage tank is provided above the spray chamber, and wherein the control circuit is provided on a panel mounted above the spray chamber and wherein the control circuit includes a supply line for a connection to a conventional alternating current supply, a junction box to which the supply line is connected and a transformer connected to the junction box, wherein the transformer and the junction box are provided with a weatherproof enclosure and the transformers transform supply voltage to a lower voltage.

14. An apparatus as claimed in claim 13, wherein the opening into the chamber opens above a centre line of the chamber and tapers inwardly.

15. An apparatus as claimed in claim 14, wherein the spray nozzles are mounted adjacent ends of the spray chamber and are directed rearwardly and inwardly towards the centre of the chamber.

16. An apparatus as claimed in claim 12, which includes a framework for supporting the spray chamber and the storage tank and an external casing surrounding the framework, the storage tank and the spray chamber, with the opening for the spray chamber extending through the casing into the spray chamber, and wherein the control circuit is provided on a panel below the spray chamber and the opening and wherein the control circuit includes a supply line for a connection to a conventional alternating current supply, a junction box to which the supply line is connected and a transformer connected to a junction box, wherein the transformer and the junction box are provided with a weatherproof enclosure and the transformer transforms the supply voltage to a lower voltage.

17. An apparatus as claimed in claim 3, wherein the storage tank is provided with a disinfecting solution comprising:
   1.6–2% N-alkyl dimethyl benzyl ammonium chloride;
   1.6–2% didecyl dimethyl ammonium chloride;
   0.2–0.4% lauramine oxide;
   0.2–0.6% tetrasodium salt of EDTA;
   4% glycerin; and water, the amount of water forming the balance of the composition.

18. An apparatus as claimed in claim 1, wherein the housing comprising an upper portion above the spray zone and a lower portion below the spray zone, wherein the spray zone is generally concave and extends rearwardly between the upper and lower portions, and wherein the lower portion provides the collection portion.

19. An apparatus as claimed in claim 18, wherein the collection portion is generally trough-shaped and extends transversely and includes retaining means to prevent excess liquid spilling out of the collection portion.

20. An apparatus as claimed in claim 19, wherein said retaining means comprises one of: lips at both ends of the trough-shaped collection portion; and the lower-most portion of the collection portion being dish-shaped, and wherein an outlet drain is provided at the bottom of the collection portion to drain off excess liquid.

21. An apparatus as claimed in claim 18, 19 or 20 wherein the spray zone has a generally uniform cross-section from one side of the apparatus to the other and is open at either side of the apparatus.

22. An apparatus as claimed in claims 18, 19 or 20, which includes two lower spray nozzles mounted on the lower portion and directed upwardly and rearwardly, and at least one upper spray nozzle mounted on the upper portion and directed downwardly and rearwardly.

23. An apparatus as claimed in claim 20, wherein the upper portion comprises a generally convexly-shaped wall, wherein the lower portion is defined by a lower convexly-shaped wall, and wherein a concavely-shaped wall extends between the upper and lower convexly-shaped walls, the collection portion comprising a lower-most portion of the concavely-shaped wall and at least part of the lower convexly-shaped wall.

24. An apparatus as claimed in claim 23, which includes two nozzles mounted on the lower portion and directed rearwardly and upwardly and at least one nozzle mounted on the upper portion and directed downwardly and rearwardly.

25. An apparatus as claimed in claim 24, wherein the concavely-shaped wall has a uniform curvature centered on an axis of curvature, wherein the spray nozzles are generally directed towards the axis of curvature, and wherein the two lower-most spray nozzles are directed inwardly.

26. An apparatus as claimed in claim 25, wherein the housing includes generally planar side walls having forward edges shaped to correspond to the profiles of the upper and lower convexly-shaped wall and the concavely-shaped wall, and wherein the housing includes a planar top surface, a planar base and a generally planar rear surface.

27. An apparatus for disinfecting a user's hands, the apparatus comprising:
   a housing defining a spray zone, the spray zone being substantially open at the front thereof to enable a user to insert both hands and to manipulate both hands within the spray zone without contacting the housing, the housing including a collection portion for collecting excess spray from the spray zone;
   a spray means comprising a plurality of spray nozzles mounted on the housing and directed rearwardly away from the front of the spray zone, for generating a spray of a liquid within the spray chamber and mounted on the drum;
   a supply means for supplying a liquid to the spray means;
   a valve means connected between the supply means and the spray means for controlling supply of the cleaning liquid;
   a sensor means mounted on the spray chamber, for sensing the presence of a user's hands within the spray chamber; and
   a control circuit including a first timer and connected to the sensor means and the valve means, the control circuit being adapted to open the valve means to supply the liquid to the spray means when the sensor means detects the presence of a user's hands and maintaining the valve means open for a period determined by the first timer, and wherein the first timer is set to supply liquid to the spray for a period in the range of 0.2 to 1.2 sec.

28. An apparatus for disinfecting a user's hands, the apparatus comprising:
   a spray zone having an axis and being disposed generally horizontally;
   an elongate opening in the front of the spray chamber, and providing access from the exterior to the interior of the chamber, to enable a user to insert both hands into the interior of the chamber, without contacting a periphery of the opening, the opening being located above the axis of the spray chamber and inclined downwardly and rearwardly, to promote drainage of liquid back into the chamber;

a spray means comprising a plurality of spray nozzles directed into the spray chamber and rearwardly away from the opening;

a supply means for supplying a liquid to the spray means;

a valve means connected between the supply means and the spray means for controlling supply of the liquid;

a sensor means mounted on the spray chamber, for sensing the presence of a user's hands within the spray chamber; and a control circuit including a first timer and connected to the sensor means and the valve means, the control circuit opening the valve means to supply the liquid to the spray means when the sensor means detects the presence of a user's hands and maintaining the valve means open for a period determined by the first timer;

wherein the period set by the first timer and the flow rate from the spray nozzles are such that the volume of liquid sprayed onto a user's hands is in the range 3 to 5 cc.

29. An apparatus as claimed in claim 28, wherein the spray nozzles comprise fog nozzles for forming a fine mist.

30. An apparatus as claimed in claim 28 or 29, wherein there are two spray nozzles directed rearwardly and towards one another, and wherein the two spray nozzles are configured to provide a total flow rate in the range 2.5 to 3.2 GPH, and wherein the first timer sets the period in the range 0.2 to 1.2 sec, and wherein the second timer sets the period in the range 5 to 10 sec.

* * * * *

UNITED STATES PATENT AND TRADEMARK OFFICE
CERTIFICATE OF CORRECTION

PATENT NO. : 6,431,189 B1
APPLICATION NO. : 09/335761
DATED : August 13, 2002
INVENTOR(S) : Ronald Henry Deibert It is certified that error appears in the above-identified patent and that said Letters Patent is hereby corrected as shown below:

Col. 9, lines 46, 48, 51, 53 and 56, in claim 1 and also Independent claim 27 reference to "spray zone", delete "zone" and add --spray chamber--

In claim 1, at column 9, lines 48 and 49, delete "being substantially open" and replace with --having an opening--.

In claim 1, at column 9, line 58, delete the term "drum" and replace with --housing--.

In claim 27, at column 12, line 42, delete the term "drum" and replace with --housing--.

In claim 8, at column 10, line 36, before the word "relay" add --first--.

In claim 10, column 10, lines 49 and 50 delete the words "spray chamber" and add --housing--.

In claim 13, column 11, line 5, after the word "current supply" add the word --voltage--.

In claim 18, column 11, line 45 replace the word "comprimising" and insert --comprimises--.

In claim 28, column 12, line 62, delete the word "zone" and add --chamber--.

In claim 30, column 14, lines 15 and 16, delete "and wherein......5 to 10 sec"

Signed and Sealed this

Thirty-first Day of July, 2007

JON W. DUDAS
*Director of the United States Patent and Trademark Office*